(12) United States Patent
Gao et al.

(10) Patent No.: US 11,932,818 B2
(45) Date of Patent: Mar. 19, 2024

(54) TAIL GAS OF GAS FERMENTATION TO DRY GASIFICATION FEEDSTOCK

(71) Applicant: LanzaTech, Inc., Skokie, IL (US)

(72) Inventors: Allan Haiming Gao, Skokie, IL (US); Robert John Conrado, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 17/180,619

(22) Filed: Feb. 19, 2021

(65) Prior Publication Data

US 2021/0284926 A1    Sep. 16, 2021

Related U.S. Application Data

(60) Provisional application No. 62/990,148, filed on Mar. 16, 2020.

(51) Int. Cl.
*C12M 1/107* (2006.01)
*C10J 3/86* (2006.01)

(52) U.S. Cl.
CPC ............ *C10J 3/86* (2013.01); *C12M 21/04* (2013.01); *C10J 2300/0923* (2013.01); *C10J 2300/0946* (2013.01); *C10J 2300/0956* (2013.01); *C10J 2300/1223* (2013.01); *C10J 2300/1681* (2013.01); *C10J 2300/1807* (2013.01)

(58) Field of Classification Search
CPC . Y02E 50/10; Y02E 50/30; C12P 7/08; C12P 7/065; C10J 2300/1681; C10J 2300/0946; C10J 2300/092; C10J 2300/0916; C10J 2300/0909; C12M 21/12; C12M 43/00; C12M 21/04; C12M 47/18; Y02P 20/145; Y02P 20/59; Y02P 30/20
See application file for complete search history.

(56) References Cited

U.S. PATENT DOCUMENTS

2008/0115415 A1    5/2008  Agrawal et al.
2008/0220489 A1*   9/2008  Offerman ............... C10L 1/023
                                                          435/157
(Continued)

FOREIGN PATENT DOCUMENTS

CN          109055438 A  *  12/2018

OTHER PUBLICATIONS

International Search Report and Written Opinion issued in corresponding International Application No. PCT/US2021/020799, dated Jun. 23, 2021, 9 pages.

(Continued)

*Primary Examiner* — Imran Akram

(57) ABSTRACT

The disclosure provides for the integration of a gas fermentation process with a gasification process whereby tail gas from the gas fermentation process is recycled to a dryer of the gasification process. The tail gas from the gas fermentation process is utilized to generate heat which in turn is used to dry feedstock to the gasification process. The heat is typically used to heat a drying gas, such as air, which is then directly or indirectly contacted with the gasification feedstock to dry the gasification feedstock. Dried gasification feedstock provides improved yield and improved quality of syngas as compared to gasification feedstock that is not dried.

18 Claims, 3 Drawing Sheets

(56) References Cited

U.S. PATENT DOCUMENTS

| | | | | |
|---|---|---|---|---|
| 2009/0031615 | A1* | 2/2009 | Joshi | C10G 2/32 |
| | | | | 422/600 |
| 2010/0156104 | A1* | 6/2010 | Bottinelli | C10J 3/20 |
| | | | | 422/600 |
| 2011/0104770 | A1* | 5/2011 | Tobey | C12P 7/52 |
| | | | | 435/141 |
| 2011/0138684 | A1 | 6/2011 | Kranz | |
| 2011/0218254 | A1* | 9/2011 | Chakravarti | C10J 3/463 |
| | | | | 518/700 |
| 2012/0122194 | A1* | 5/2012 | Dumons | C10J 3/00 |
| | | | | 435/262 |
| 2013/0137151 | A1* | 5/2013 | Tobey | C01B 3/36 |
| | | | | 252/373 |
| 2015/0024448 | A1* | 1/2015 | Djadali | C12P 7/16 |
| | | | | 435/163 |
| 2015/0225749 | A1 | 8/2015 | Hickey | |
| 2016/0208290 | A1* | 7/2016 | Foody | C12P 7/54 |
| 2019/0002930 | A1* | 1/2019 | Foody | C12P 7/10 |
| 2019/0185887 | A1* | 6/2019 | Foody | C01B 3/16 |

OTHER PUBLICATIONS

Chiba, Section 18: Diet Formulation and Common Feed Ingredients, Animal Nutrition Handbook, 2nd revision, pp. 481-531, 2009.

Dong, J., Chi, Y., Tang, Y. Ni, M. Nzihou, A., Weiss-Hortala, E. Huang, Q. (2016) Effect of operating parameters and moisture content on municipal solid waste pyrolysis and gasification. Energy & Fuels, 30(5), 3994-4001.

Drake, Acetogenic Prokaryotes, In: The Prokaryotes, 3rd edition, p. 354, New York, NY, 2006.

Li, H. Chen, Q., Zhang, X. Finney, K. N., Sharifi, V.N., Swithenbank, J. (2012) Evaluation of a biomass drying process using waste heat from process industries: A case study. Applied Thermal Engineering, 35, 71-80.

Ragsdale, Biochim Biophys Acta, 1784: 1873-1898, 2008.

* cited by examiner

TAIL GAS OF GAS FERMENTATION TO DRY GASIFICATION FEEDSTOCK

CROSS REFERENCE TO RELATED APPLICATIONS

This application claims the benefit of U.S. Provisional Patent Application No. 62/990,148 filed Mar. 16, 2020, the entirety of which is incorporated herein by reference.

FIELD OF THE DISCLOSURE

The disclosure relates to processes for improving the integration of gas fermentation and gasification. In particular, the disclosure relates to the recycling at least a portion of the tail gas of the gas fermentation process to a dryer for the feedstock for the gasification process.

BACKGROUND

As the world population increases, the waste generated by such a population becomes a growing concern. One solution for waste disposal is gasification. Gasification is a process that converts organic or fossil fuel-based carbonaceous materials into syngas comprising carbon monoxide, carbon dioxide, and hydrogen. Gasification advantageously both reduces the amount of waste that ends up in a landfill and produces a product, syngas, which can be converted by one or more subsequent process to useful products.

Syngas produced by gasification may be utilized by a number of processes including Fischer-Tropsch. The Fischer-Tropsch process provides for the catalytic hydrogenation of carbon monoxide to produce a variety of products including hydrocarbons, alcohols, or other oxygenated hydrocarbons. However, the catalytic beds within the Fischer-Tropsch process are particularly sensitive to various components which may be in the syngas stream depending on the gasification feedstock. One such component is sulfur. If sulfur is not removed from the syngas stream prior to being sent to the Fischer-Tropsch process, the sulfur can deactivate the catalysts required for the Fischer-Tropsch reaction. Thus, in order to arrive at a suitable gas for the Fischer-Tropsch process, extensive gas clean-up technology is often required.

One alternative to the Fischer-Tropsch process is gas fermentation. Gas fermentation provides for the biological fixation of gases, including syngas, into one or more product. Gas fermentation has a variety of advantages over the Fischer-Tropsch process. Firstly, Fischer-Tropsch utilizes high temperatures (150-350° C.), elevated pressures (30 bar), and heterogeneous catalysts such as cobalt, ruthenium, and iron. In comparison, gas fermentation takes places at about 37° C. and is often conducted at atmospheric pressure, which presents significant energy and cost savings relative to the Fischer-Tropsch process. Additionally, the Fischer-Tropsch process requires a relatively fixed $H_2$:CO ratio in the syngas, around 2:1, whereas gas fermentation is capable of receiving and utilizing a diverse range of substrates with varying $H_2$:CO ratios.

When integrating gasification to produce syngas and gas fermentation, actions may be taken to control the type of syngas produced. For example, drying of biomass has been discussed in Li, H. Chen, Q., Zhang, X. Finney, K. N., Sharifi, V. N., Swithenbank, J. (2012) Evaluation of a biomass drying process using waste heat from process industries: A case study. Applied Thermal Engineering, 35, 71-80. In the field of pyrolysis and gasification, operating parameters and moisture content was studied in Dong, J., Chi, Y., Tang, Y. Ni, M. Nzihou, A., Weiss-Hortala, E. Huang, Q. (2016) Effect of operating parameters and moisture content on municipal solid waste pyrolysis and gasification. Energy & Fuels, 30(5), 3994-4001.

However, there remains a need for a higher level of integration between a gasification operation and gas fermentation operation so that a waste stream of one operation is used in the most beneficial way by the other operation. An unexpectedly beneficial use of the tail gas from the gas fermentation operation is to employ at least a portion of the tail gas to heat a drying gas which in turn is used to dry the feedstock of the gasification operation. Drying the feedstock of the gasification operation provides higher yield and higher quality syngas which thereby increases the system wide production of a desired product from an integrated gasification and gas fermentation operation. Surprisingly, from an energy perspective, the recovery of energy from the tail gas is substantially greater when used for drying feedstock as compared to generating electricity or steam.

BRIEF SUMMARY

The disclosure involves a method comprising heating a drying gas; providing the heated drying gas to a dryer containing a gasification feedstock to generate a dried gasification feedstock; gasifying at least a portion of the dried gasification feedstock to generate syngas; fermenting at least a portion of the syngas in a bioreactor using a microorganism to generate at least one product and tail gas; and utilizing at least a portion of the tail gas to provide heat for heating the drying gas. In an embodiment the gasification feedstock is municipal solid waste, agricultural waste, microbial biomass, or any combination thereof. In an embodiment, the tail gas comprises carbon dioxide, carbon monoxide, hydrogen, nitrogen, and methane.

The disclosure further involves an apparatus comprising: a dryer having one or more burners for heating a drying gas, the dryer in communication with a feedstock conduit; a gasifier in communication with the dryer; a bioreactor in fluid communication with the gasifier; a product conduit and a tail gas conduit in fluid communication with the bioreactor; and the tail gas conduit also in fluid communication with the one or more burners.

In one embodiment, the fermentation process utilizes one or more C1-fixing microorganisms, suitable to ferment C1-containing gaseous substrate, such as syngas produced through gasification. In various embodiments, the C1-fixing microorganism is selected from the group consisting of *Moorella, Clostridium, Ruminococcus, Acetobacterium, Eubacterium, Butyribacterium, Oxobacter, Methanosarcina,* and *Desulfotomaculum.* The microorganism may be a member of the genus *Clostridium.* In certain instances, the microorganism is *Clostridium autoethanogenum.*

In various embodiments, the gasification feedstock is municipal solid waste, industrial solid waste, agricultural waste, lignocellulosic material, microbial biomass, or any combination thereof. The gasification feedstock is dried in a dryer and then gasified to produce a syngas stream. At least a portion of the syngas stream is passed to the fermentation process to produce one or more product and possibly at least one by-product. In some embodiments, the microbial biomass generated from the fermentation process is passed to the gasification operation as feedstock to the gasification.

In some embodiments, substantially all of the microbial biomass produced by the fermentation process is either recycled to the fermentation process following product recovery, treated by the wastewater treatment process and/or sent to the gasification process to produce syngas. In certain instances, the gasification process receives at least 20%, at least 30%, at least 40%, at least 50%, at least 60%, at least 70%, at least 80%, at least 90%, or substantially all of the microbial biomass from the fermentation process.

In some embodiments, the microbial biomass generated from the wastewater treatment process is sent to the gasification process. The microbial biomass generated from the wastewater treatment process may, at least in part, be recovered from the anaerobic digester process within the wastewater treatment process. In various instances, at least a portion of the microbial biomass from the wastewater treatment process is dried prior to being passed to the gasification process. In certain instances, substantially all of the microbial biomass from the wastewater treatment process is dried prior to being passed to the gasification process.

In particular embodiments, at least a portion of the microbial biomass depleted water from the fermentation process is sent to the gasification process. In various instances, the microbial biomass depleted water is sent to the gasification process to increase the $H_2$:CO ratio in the syngas stream. Preferably, at least a portion of the microbial biomass depleted water is sent to the gasification process to increase the $H_2$:CO ratio in the syngas stream to at least 2:1, at least 3:1, or at least 4:1. Sending the microbial biomass depleted water to the gasification process, where the $H_2$:CO ratio in the syngas stream is increased, may result in increased selectivity to ethanol produced by the gas fermentation process, decreased selectivity to microbial biomass production, decreased water consumption by the fermentation reaction, and/or a reduced bleed flow to the wastewater treatment process.

In particular embodiments, at least a portion of wastewater generated from the fermentation process is sent to the gasification process. This wastewater may contain one or more product and/or by-product including but not limited to microbial biomass. In various instances, the wastewater generated from the fermentation process is sent to the gasification process to increase the $H_2$:CO ratio in the syngas stream. Preferably, at least a portion of the wastewater generated from the fermentation process is sent to the gasification process to increase the $H_2$:CO ratio in the syngas stream to at least 2:1, at least 3:1, or at least 4:1. Sending the wastewater generated from the fermentation process to the gasification process, where the $H_2$:CO ratio in the syngas stream is increased, may result in increased selectivity to ethanol produced by the gas fermentation process, decreased selectivity to microbial biomass production, decreased water consumption by the fermentation reaction, and/or a reduced bleed flow to the wastewater treatment process.

In particular embodiments, at least a portion of the clarified water from the wastewater treatment process is sent to the gasification process. In various instances, the clarified water from the wastewater treatment process is sent to the gasification process to increase the $H_2$:CO ratio in the syngas stream. Preferably, at least a portion of the clarified water from the wastewater treatment process is sent to the gasification process to increase the $H_2$:CO ratio in the syngas stream to at least 2:1, at least 3:1, or at least 4:1. Sending the clarified water from the wastewater treatment process to the gasification process, where the $H_2$:CO ratio in the syngas stream is increased, may result in increased selectivity to ethanol produced by the gas fermentation process, decreased selectivity to microbial biomass production, decreased water consumption by the fermentation reaction, and/or a reduced bleed flow to the wastewater treatment process.

Preferably, at least a portion of at least one effluent from the fermentation process and/or the wastewater treatment process replaces at least a portion of the process water required by the gasification process. In certain instances, the process water required by the gasification process is reduced by at least 45 percent. In at least one embodiment, the process water required by the gasification process is reduced between 45 to 100 percent. In certain embodiments, the process water required by the gasification process is reduced between 45 and 75 percent, 55 to 75 percent, 65 to 75 percent, 55 to 100 percent, 65 to 100 percent, or 75 to 100 percent.

In certain instances, at least a portion of at least one effluent is injected into the syngas stream produced by the gasification process to reduce the temperature of the syngas stream. Preferably, the effluent injected into the syngas stream produced by the gasification process is selected from the group consisting of: microbial biomass depleted water, wastewater generated from the fermentation process, and clarified water from the wastewater treatment plant. Preferably the temperature of the syngas stream is reduced by at least 100 degrees Celsius. In at least one embodiment, the syngas stream exiting the gasification process is between 800° C. and 1200° C. Preferably, the temperature of the syngas stream is reduced within a temperature range suitable for further gas treatment and/or fermentation. In various instances, the injection of at least one effluent into the syngas stream is completed to remove at least one particulate from the syngas stream.

In certain instances, the syngas stream is partially quenched. Preferably, the syngas stream is partially quenched by injecting one or more effluent into the syngas stream, the one or more effluent selected from the group consisting of microbial biomass depleted water, wastewater generated from the fermentation process, and clarified water from the wastewater treatment plant. In various embodiments, a partial quench of the syngas stream reduces the temperature of the syngas stream to 700-800° C. In various embodiments, this reduction in temperature requires approximately 1.2 tonnes of process water per 10,000 $Nm^3$ of quenched syngas, starting at 1000° C. Preferably, at least 20%, at least 30%, at least 40%, at least 50%, at least 60%, at least 70%, at least 80%, at least 90%, or substantially all of this process water is replaced through the injection of one or more effluent into the syngas stream.

In certain instances, the syngas stream is fully quenched. Preferably, the syngas stream is fully quenched by injecting one or more effluent into the syngas stream, the one or more effluent selected from the group consisting of microbial biomass depleted water, wastewater generated from the fermentation process, and clarified water from the wastewater treatment plant. In various embodiments, a full quench of the syngas stream reduces the temperature of the syngas stream to less than 300° C. In various embodiments, this reduction in temperature requires approximately 4 tonnes of process water per 10,000 $Nm^3$ of quenched syngas, starting at 1000° C. Preferably, at least 20%, at least 30%, at least 40%, at least 50%, at least 60%, at least 70%, at least 80%, at least 90%, or substantially all of this process water is replaced through the injection of one or more effluent into the syngas stream.

In particular embodiments, at least a portion of biogas generated from the wastewater treatment process is sent to the gasification process. This biogas may contain one or more component selected from the group consisting of methane, carbon dioxide, carbon monoxide, ammonia, and a sulfur compound. In various instances, this sulfur compound is hydrogen sulfide. In at least one embodiment, the biogas comprises approximately 60 percent methane and approximately 40 percent carbon dioxide. In at least one embodiment, the biogas comprises approximately 65 percent methane and approximately 35 percent carbon dioxide.

In particular embodiments, at least a portion of biogas generated from the wastewater treatment process is used as a heating source. Preferably, at least a portion of the biogas generated from the wastewater treatment process is used as a heating source by the gasification process. In various instances, at least a portion of the biogas sent to the gasification process is used as a heating source for melting at least a portion of the slag produced by the gasification process. In one or more embodiment, the biogas from the wastewater treatment process is sent to a removal process prior to being sent to the gasification process. In various instances, the removal process comprises one or more removal unit capable of removing, converting and/or reducing the amount of at least one constituent in the biogas stream. Preferably, the removal process removes at least a portion of at least one sulfur compound from the biogas stream before the biogas stream is sent to the gasification process.

In particular embodiments, at least a portion of the methane within the biogas is reformed into CO and $H_2$ upon being gasified by the gasification process. In various instances, the methane reacts with the moisture contained in the syngas to produce carbon monoxide and hydrogen.

In an embodiment, at least a portion of the tail gas generated from the fermentation process, unused syngas generated by the gasification process, crude ethanol from the product recovery process, and/or fusel oil from the product recovery process are used as a heating source. Preferably, at least a portion of at least one of these effluents is used as a heating source by the gasification process. In various instances, at least a portion of at least one of these effluents is sent to the gasification process to be used as a heating source for melting at least a portion of the slag produced by the gasification process. In one or more embodiment, these effluent is treated by a removal process prior to being sent to the gasification process. In various instances, the removal process comprises one or more removal unit capable of removing, converting and/or reducing the amount of at least one constituent in the effluent.

In addition to passing at least a portion of the clarified water from the wastewater treatment process to the gasification process, at least a portion of the clarified water from the wastewater treatment process may be passed to the fermentation process. In particular instances, substantially all of the clarified water from the wastewater treatment process is recycled to either the gasification process and/or the fermentation process. In certain instances, the gasification process receives at least 10%, at least 20%, at least 30%, at least 40%, at least 50%, at least 60%, at least 70%, at least 80%, at least 90%, or substantially all of the clarified water from the wastewater treatment process. In certain instances, the fermentation process receives at least 10%, at least 20%, at least 30%, at least 40%, at least 50%, at least 60%, at least 70%, at least 80%, at least 90%, or substantially all of the clarified water from the wastewater treatment process.

Preferably, the fermentation process utilizes at least a portion of the syngas from the gasification process to produce one or more fuels or chemicals. At least one of the products produced by the fermentation process may be selected from the group comprising: ethanol, acetate, butanol, butyrate, 2,3-butanediol, 1,3-butanediol, lactate, butene, butadiene, methyl ethyl ketone, ethylene, acetone, isopropanol, lipids, 3-hydroypropionate, terpenes (including but not limited to isoprene), fatty acids, 2-butanol, isobutylene, isobutanol, 1,2-propanediol, 1-propanol, and C6-C12 alcohols.

In one or more embodiment, at least a portion of the microbial biomass produced by the fermentation process may be converted to a single cell protein (SCP).

In various instances, at least a portion of the one or more fuels or chemicals is sent to a secondary conversion process. Preferably, the secondary conversion process further converts at least a portion of one or more fuels or chemicals to at least one component of diesel fuel, jet fuel, gasoline, propylene, nylon 6-6, rubber, and/or resins.

In one or more embodiment, the syngas from the gasification process is sent to a removal process prior to being sent to the fermentation process. In various instances, the removal process comprises one or more removal unit capable of removing, converting and/or reducing the amount of microbe inhibitors and/or catalyst inhibitors contained in the syngas stream.

Preferably, at least one constituent removed, converted, and or reduced in the syngas stream by the removal process is selected from the group comprising: sulphur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars.

Preferably, the removal process comprises least one removal unit be selected from the group comprising: hydrolysis unit, acid gas removal unit, deoxygenation unit, catalytic hydrogenation unit, particulate removal unit, chloride removal unit, tar removal unit, and hydrogen cyanide polishing unit. In various instances, the removal process comprises at least two removal units.

The disclosure may further provide for the increase and/or decrease of pressure of the syngas stream at one or more points in the process.

DETAILED DESCRIPTION

Figure 1:
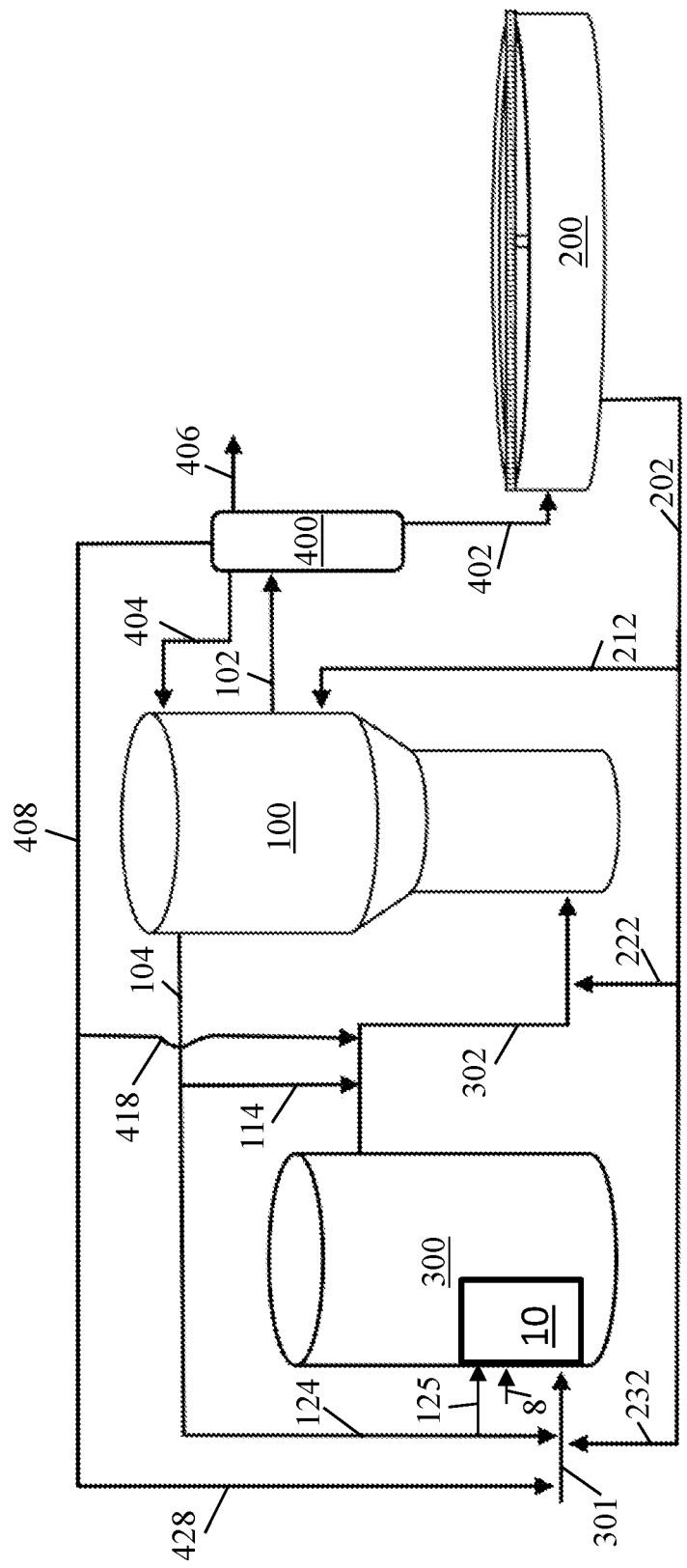
FIG. 1 shows a process integration scheme depicting the integration of a gasification process, a gas fermentation process, a product recovery process, and a wastewater treatment process, in accordance with one embodiment of the disclosure.

The disclosure describes an integration of a gasification process and a fermentation process and optionally a wastewater treatment process. Tail gas from the fermentation process is recycled to the gasification process as fuel for the burners in the feed stock dryer of the gasification process thereby providing substantial unexpected benefits to the efficiencies and synergies to the integrated processes.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, increasing the volume of desired product produced per volume of substrate consumed, increasing the rate of production or level of production of the desired product, increasing the relative proportion of the desired product produced compared with other by-products of the fermentation, decreasing the amount of water consumed by the process, and decreasing the amount of energy utilized by the process.

The terms "increasing the efficiency", "increased efficiency" and the like, when used in relation to the gasification process, include, but are not limited to, increasing the amount of syngas produced by the process, decreasing the amount of water supply utilized by the process, optimization of the syngas stream for gas fermentation, decreasing the greenhouse gas emissions, and decreasing the amount of energy, including but not limited to external fuel, utilized by the process.

The terms "increasing the efficiency", "increased efficiency" and the like, when used in relation to the wastewater treatment process, include, but are not limited to, decreasing the holdup time of water within the process, increasing the utilization of biogas generated by the process, decreasing the amount of effluent sent to the wastewater treatment process, decreasing the volume requirement of the process, decreasing the need for ammonia separation by the process, and decreasing the amount of energy utilized by the process.

The term "fermentation", "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous". "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

The term "wastewater treatment" and the like should be interpreted as the process that separates components from the effluent from the fermentation process to produce a clarified water. The wastewater treatment process may include, but is not limited to, one or more anaerobic digesters, with varying residence times, and one or more ammonia stripping process.

The term "gasification" and the like should be interpreted as the process that converts organic and/or fossil fuel based carbonaceous materials into carbon monoxide (CO), hydrogen ($H_2$), and carbon dioxide ($CO_2$). The gasification process may include various technologies including but not limited to, counter-current fixed bed gasifiers, co-current fixed bed gasifiers, fluidized bed reactors, entrained flow gasifiers, and plasma gasifiers. The gasification process may utilize any feed, which can produce a syngas stream. The term "gasification process" encompasses the gasifier itself along with unit operations associated with gasification, including the heating source for the gasifier and syngas quench processes.

"Syngas stream", "synthesis stream" and the like refers to the gaseous substrate exiting the gasification process. The syngas stream should primarily be composed of carbon monoxide (CO), hydrogen ($H_2$), and carbon dioxide ($CO_2$). The composition of the syngas stream can vary significantly depending on the feedstock and the gasification process involved; however the typical composition of syngas includes thirty to sixty percent (30-60%) carbon monoxide (CO), twenty-five to thirty percent (25-30%) hydrogen ($H_2$), zero to five percent (0-5%) methane ($CH_4$), five to fifteen percent (5-15%) carbon dioxide ($CO_2$), plus a lesser or greater amount of water vapor, smaller amounts of sulphur compounds, hydrogen sulphide ($H_2S$), carbonyl sulphide (COS), ammonia ($NH_3$), and other trace contaminants.

In particular embodiments, the presence of hydrogen results in an improved overall efficiency of alcohol production by the fermentation process.

Syngas composition can be improved to provide a desired or optimum $H_2:CO:CO_2$ ratio. The syngas composition may be improved by adjusting the feedstock being fed to the gasification process. The desired $H_2:CO:CO_2$ ratio is dependent on the desired fermentation product of the fermentation process. For ethanol, the optimum $H_2:CO:CO_2$ ratio would be:

$$(x):(y):\left(\frac{x-2y}{3}\right),$$

where x>2y, in order to satisfy the stoichiometry for ethanol production

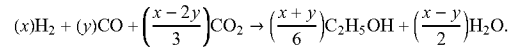

Operating the fermentation process in the presence of hydrogen has the added benefit of reducing the amount of $CO_2$ produced by the fermentation process. For example, a gaseous substrate comprising minimal $H_2$ will typically produce ethanol and $CO_2$ by the following stoichiometry [$6CO+3H_2O \rightarrow C_2H_5OH+4CO_2$]. As the amount of hydrogen utilized by the C1-fixing bacterium increases, the amount of $CO_2$ produced decreases [e.g., $2CO+4H_2 \rightarrow C_2H_5OH+H_2O$].

When CO is the sole carbon and energy source for ethanol production, a portion of the carbon is lost to $CO_2$ as follows:

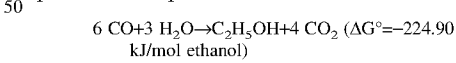

As the amount of $H_2$ available in the substrate increases, the amount of $CO_2$ produced decreases. At a stoichiometric ratio of 2:1 ($H_2:CO$), $CO_2$ production is completely avoided.

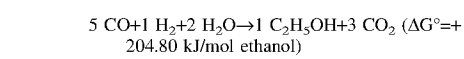

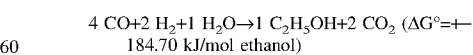

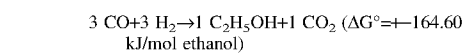

"Stream" refers to any substrate which is capable of being passed, for example, from one process to another, from one unit to another, and/or from one process to a carbon capture means.

"Reactants" as used herein refer to a substance that takes part in and undergoes change during a chemical reaction. In particular embodiments, the reactants include but are not limited to CO and/or $H_2$.

"Microbe inhibitors" as used herein refer to one or more constituent that slows down or prevents a particular chemical reaction or another process including the microbe. In particular embodiments, the microbe inhibitors include, but are not limited to, oxygen ($O_2$), hydrogen cyanide (HCN), acetylene ($C_2H_2$), and BTEX (benzene, toluene, ethylbenzene, xylene).

"Catalyst inhibitor", "adsorbent inhibitor", and the like, as used herein, refer to one or more substance that decreases the rate of, or prevents, a chemical reaction. In particular embodiments, the catalyst and/or adsorbent inhibitors may include but are not limited to, hydrogen sulfide ($H_2S$) and carbonyl sulfide (COS).

"Removal process", "removal unit", "clean-up unit", and the like includes technologies that are capable of either converting and/or removing microbe inhibitors and/or catalyst inhibitors from the gas stream. In particular embodiments, catalyst inhibitors must be removed by an upstream removal unit in order to prevent inhibition of one or more catalyst in a downstream removal unit.

The term "constituents", "contaminants", and the like, as used herein, refers to the microbe inhibitors, and/or catalyst inhibitors that may be found in the gas stream. In particular embodiments, the constituents include, but are not limited to, sulphur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars.

The term "treated gas", "treated stream" and the like refers to the gas stream that has been passed through at least one removal unit and has had one or more constituent removed and/or converted.

The term "carbon capture" as used herein refers to the sequestration of carbon compounds including $CO_2$ and/or CO from a stream comprising $CO_2$ and/or CO and either:
  converting the $CO_2$ and/or CO into products; or
  converting the $CO_2$ and/or CO into substances suitable for long-term storage; or
  trapping the $CO_2$ and/or CO in substances suitable for long-term storage;
  or a combination of these processes.

The term "bioreactor", "reactor" and the like includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor is preferably adapted to receive a gaseous substrate comprising CO or $CO_2$ or $H_2$ or mixtures thereof. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

"Nutrient media" or "Nutrient medium" is used to describe bacterial growth media. Preferably the fermentation process utilizes nutrient medium within the bioreactor. Generally, this term refers to a media containing nutrients and other components appropriate for the growth of a microbial culture. The term "nutrient" includes any substance that may be utilized in a metabolic pathway of a microorganism. Exemplary nutrients include potassium, B vitamins, trace metals, and amino acids.

The term "fermentation broth" or "broth" is intended to encompass the mixture of components including nutrient media and a culture or one or more microorganisms. Preferably the fermentation process utilizes fermentation broth to ferment the syngas stream to one or more product.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "desired composition" is used to refer to the desired level and types of components in a substance, such as, for example, of a gas stream, including but not limited to syngas. More particularly, a gas is considered to have a "desired composition" if it contains a particular component (e.g. CO, $H_2$, and/or $CO_2$) and/or contains a particular component at a particular proportion and/or does not contain a particular component (e.g. a contaminant harmful to the microorganisms) and/or does not contain a particular component at a particular proportion. More than one component may be considered when determining whether a gas stream has a desired composition.

Unless the context requires otherwise, the phrases "fermenting", "fermentation process" or "fermentation reaction" and the like, as used herein, are intended to encompass both the growth phase and product biosynthesis phase of the gaseous substrate.

A "microorganism" is a microscopic organism, especially a bacterium, archea, virus, or fungus. The microorganism of the disclosure is typically a bacterium. As used herein, recitation of "microorganism" should be taken to encompass "bacterium." It should be noted that the term microorganism and the term bacteria are used interchangeably throughout the document.

A "parental microorganism" is a microorganism used to generate a microorganism of the disclosure. The parental microorganism may be a naturally-occurring microorganism (e.g., a wild-type microorganism) or a microorganism that has been previously modified (e.g., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In an embodiment, the parental microorganism is *Clostridium autoethanogenum* LZ1561, which was deposited on Jun. 7, 2010, with Deutsche Sammlung von Mikroorganismen and Zellkulturen GmbH (DSMZ) located at Inhoffenstraße 7B, D-38124 Braunschweig, Germany on Jun. 7, 2010, under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism. In one embodiment, the microorganism of the disclosure is derived from *Clostridium autoethanogenum*, *Clostridium ljungdahlii*, or *Clostridium ragsdalei*. In an embodiment, the microorganism of the disclosure is derived from *Clostridium autoethanogenum* LZ1561, which is deposited under DSMZ accession number DSM23693.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the disclosure is a C1-fixing bacterium.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the disclosure is an anaerobe.

"Acetogens" are obligately anaerobic bacteria that use the Wood-Ljungdahl pathway as their main mechanism for energy conservation and for the synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the disclosure is an acetogen.

An "ethanologen" is a microorganism that produces or is capable of producing ethanol. Typically, the microorganism of the disclosure is an ethanologen.

An "autotroph" is a microorganism capable of growing in the absence of organic carbon. Instead, autotrophs use inorganic carbon sources, such as CO and/or $CO_2$. Typically, the microorganism of the disclosure is an autotroph.

A "carboxydotroph" is a microorganism capable of utilizing CO as a sole source of carbon and energy. Typically, the microorganism of the disclosure is a carboxydotroph.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

"Substrate" refers to a carbon and/or energy source for the microorganism of the disclosure. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$ or $N_2$.

The term "co-substrate" refers to a substance that, while not necessarily being the primary energy and material source for product synthesis, can be utilized for product synthesis when added to another substrate, such as the primary substrate.

The composition of the substrate may have a significant impact on the efficiency and/or cost of the reaction. For example, the presence of oxygen (02) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, lignin, cellulose, or hemicellulose.

The microorganism of the disclosure may be cultured with the gas stream to produce one or more products. For instance, the microorganism of the disclosure may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498). In certain embodiments, microbial biomass itself may be considered a product. These products may be further converted to produce at least one component of diesel, jet fuel, and/or gasoline. Additionally, the microbial biomass may be further processed to produce a single cell protein (SCP).

A "single cell protein" (SCP) refers to a microbial biomass that may be used in protein-rich human and/or animal feeds, often replacing conventional sources of protein supplementation such as soymeal or fishmeal. To produce a single cell protein or other product, the process may comprise additional separation, processing, or treatments steps.

For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavor, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, $3^{rd}$ revision, pages 575-633, 2014.

A "native product" is a product produced by a genetically unmodified microorganism. For example, ethanol, acetate, and 2,3-butanediol are native products of *Clostridium autoethanogenum, Clostridium ljungdahlii,* and *Clostridium ragsdalei.* A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product accounts for at least about 5%, 10%, 15%, 20%, 30%, 50%, or 75% of all fermentation products produced by the microorganism of the disclosure. In one embodiment, the target product accounts for at least 10% of all fermentation products produced by the microorganism of the disclosure, such that the microorganism of the disclosure has a selectivity for the target product of at least 10%. In another embodiment, the target product accounts for at least 30% of all fermentation products produced by the microorganism of the disclosure, such that the microorganism of the disclosure has a selectivity for the target product of at least 30%.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

Target products may be separated or purified from a fermentation broth using any suitable removal process, which may utilize a method or combination of methods known in the art, including, for example, fractional distillation, vacuum distillation, evaporation, pervaporation, gas stripping, phase separation, and extractive fermentation, including, for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells may be returned to the bioreactor. The cell-free permeate remaining after target products have been removed may also be returned to the bioreactor. Additional nutrients (such as B vitamins) may be added to the cell-free permeate to replenish the medium before it is returned to the bioreactor.

This disclosure shows that by integrating the gasification operation and the fermentation operation into an integrated system, unexpected synergies result in the overall efficiency of the integrated system being improved. More specifically, the disclosure identifies an integration where the tail gas of the fermentation operation is used to heat a drying gas that is then used to dry the feedstock to the gasification operation.

Tail gas from the fermentation process may be used for electricity or steam generation, but at best, an operator can recover about 60% of the energy of the tail gas, broken down into about 40% for electricity and about 20% for steam. Surprisingly, and in contrast to the above, using tail gas for drying feedstock to the gasification operation, an operator can recover as much as about 92% of the tail gas energy as improved yield in syngas from the gasification operation.

It has been previously shown that drying feedstock from 51.2% to 9.2% can improve cold gas efficiency, i.e., the amount of syngas generated from the gasification feedstock on an energy basis, from 45% to 70%. In addition, the energy basis of the produced syngas increases from 3.8 $MJ/Nm^3$ to 4.9 $MJ/Nm^3$, indicating that the concentration of fermentable species such as CO and $H_2$ will also increase. This has additional cost saving benefits in the downstream portions of the system including compression and fermentation. For example, this decreases specific energy usage in downstream fermentation where the more dilute gas requires the same compression and reactor volume to generate a smaller amount of ethanol product.

Furthermore, the disclosure improves syngas yield and quality which generates greater economic return as compared to using tail gas for steam generation or electricity generation. More specifically, using tail gas in drying the feed stock to a gasifier results in greater syngas production from the gasifier. Greater syngas production results in higher volume and better quality feed to the fermentation process and therefore greater product production in the fermentation process. The value of the increased quantity of product from the fermentation process exceeds the value of the electricity or the steam that would have been generated by the tail gas had the tail gas not been used in the drying operation.

A comparison of expected revenue from using the tail gas for drying feedstock to the gasifier versus using tail gas to generate electricity and stream is shown in the table below. The comparison is based on a 41.7 tonne per hour (TPH) gasifier and a 1000 tonne per day (TPD) feedstock gas fermentation unit with a feedstock energy density of 11 MJ/kg.

TABLE 1

| Tail Gas | 50 GJ/h |
| --- | --- |
| Dryer Efficiency | 3 GJ/tonne water |
| Water Removed | 6.7 tonne/h |
| Municipal solid waste Starting moisture | 40% |
| Municipal solid waste Final moisture | 23% |
| Estimated Increase in Syngas Efficiency | 16.7% Relative |
| Estimated Increase in Syngas Production | 45.9 GJ/h |
| Estimated Increase in Ethanol Production | 1.0 tonne/h |
| Value of Tail Gas @ ethanol price of $1000/tonne. | $20/GJ |

TABLE 2

| Tail Gas | 50 GJ/h |
| --- | --- |
| Cogeneration Electricity Efficiency | 40% |
| Cogeneration Steam Efficiency | 20% |
| Estimated Electrical output | 5.6 MW |
| Estimated Steam output | 4.5 tonne/h |
| Value of Tail Gas @ Electricity price of $80/MWh and steam price of $20/tonne | $10.8/GJ |

It is also noted that the tail gas may be too dilute for use in electricity generation, in which case the value of using to dry feedstock to the gasifier becomes even greater.

Other embodiments include one or more effluents selected from biogas generated from a wastewater treatment process, tail-gas generated from the fermentation process, unused syngas generated by the gasification process, microbial biomass generated from the fermentation process, microbial biomass generated from a wastewater treatment process, crude ethanol from the product recovery process, fusel oil from the product recovery process, microbial biomass depleted water, wastewater generated from the fermentation process, and clarified water from a wastewater treatment process, which may be sent to the gasification process to produce a syngas stream, used by the gasification process as a heating source, and/or used by the gasification process to quench the syngas stream. The syngas stream is preferably suitable for gas fermentation.

These various effluents are produced either in or downstream of, the fermentation process. The fermentation process produces a wastewater stream that contains organic metabolites, such as microbial biomass, ethanol, acetate, and 2-3 butanediol, and various inorganic compounds such as salts and trace metals. This wastewater stream is often sent to a wastewater treatment process. A typical wastewater treatment process includes the following steps: (i) separation of the microbial biomass, which is a suspended solid; (ii) concentration of the microbial biomass solids in a separate long residence time, approximately thirty days, anaerobic digester; (iii) concentration of the clarified effluent, with reduced amounts of microbial biomass solids, containing soluble organics, in a shorter residence time, approximately two to three days, anaerobic digester. Typically, these anaerobic digesters consumer a majority, preferably greater than eighty percent (80%) of the organic matter in the feed and produce a biogas product. The biogas product is composed primarily of methane ($CH_4$) and carbon dioxide ($CO_2$).

This biogas product may be useful for power generation. However, to use the biogas for power generation, the biogas typically must be treated by one or more removal unit. Furthermore, as later illustrated, use of microbial biomass to produce biogas was found to be a relatively low-value use of the microbial biomass when compared to the opportunities for gasifying the microbial biomass.

In addition to the aforementioned steps, the wastewater treatment process may also include additional treatment steps following the anaerobic digesters. Typically, the treated effluent from the anaerobic digesters is subjected to additional treatment including, aerobic treatment, struvite recovery, nitrogen recovery, and in some instances reverse osmosis. The clarified water produced by the wastewater treatment process is suitable for re-use and/or discharge. One suitable way to use this clarified water is to recycle the clarified water to the fermentation process and/or the gasification process.

Although the wastewater treatment process is capable of successfully treating the wastewater from the fermentation process to produce clarified water, the organic metabolites in the wastewater stream often pose several challenges. Specifically, the treatment of the microbial biomass in the wastewater stream by the wastewater treatment process can pose design challenges due to (i) the high protein content and thus high ammonia generation during anaerobic digestion, and (ii) the large plot space required to house the wastewater treatment process.

Ammonia poses a challenge to anaerobic digestion because ammonia is associated with inhibiting methanogenesis during the anaerobic digestion process if it is in high concentrations. Inhibitory concentrations of ammonia have been found to be in the range of 2 to 3 g/L. This threshold can be greatly surpassed, as digestion of separated microbial biomass can result in ammonia concentrations greater than 20 g/L. Thus, in order to process the microbial biomass by a wastewater treatment process, an ammonia stripping process is often required to lower the ammonia concentration below the inhibitory levels.

A large plot space requirement poses a significant issue in localities where land is at a premium. Each component of the wastewater treatment process requires a substantial amount of space due to the significant volumes that are processed. For example, the long residence time anaerobic digester can, in some instances, exceed 7,000 m$^3$.

The inventors have found that by recycling at least a portion of the microbial biomass to the gasification process these challenges can be overcome. With less microbial biomass being sent to anaerobic digestion, less ammonia is produced and therefore the need for an ammonia stripping process is reduced and/or eliminated. Additionally, as larger volumes of effluent from the fermentation process are sent to the gasification process, lesser volumes of effluent are sent to the wastewater treatment process. With lesser volumes of effluent being processed by the wastewater treatment process, the required volume and corresponding plot space requirements are reduced, making the design advantageous for localities where land is at a premium.

In addition to overcoming the aforementioned challenges, recycling microbial biomass to the gasification process provides the following advantageous results: (i) a greater portion of energy contained in the biomass is recovered; (ii) the H$_2$:CO ratio within the resulting syngas stream is increased; (iii) the inorganic content, metal compounds, and alkali elements in the microbial biomass, which normally would require additional treatment steps by the wastewater treatment process, are conveniently collected in the gasification process as part of the ash fraction, which already requires disposal, thus overall waste treatment is reduced; and (iv) the nitrogen contained within the biomass will undergo reaction in the gasifier to become N$_2$, NH$_3$, and trace HCN, which integrates well with existing removal processes.

The inventors have also surprisingly found revenue gain when recycling biomass to gasification when compared to the use of biomass in the production of biogas. Specifically, the inventors have found a 321% gain in revenue when comparing the utilization of biomass in syngas versus the utilization of biomass in the production of biogas.

This percentage of revenue gain is best illustrated in the table below. Table 3 shows the value generated from 20 GJ/hr of biomass, as taken through each pathway.

The conversion efficiency of producing syngas from biomass via gasification is approximately seventy-five percent (75%), which can vary depending on the gasification technology used. The GJ/hr Product Gas represents the GJ/hr Biomass multiplied by the respective conversion efficiency. The GJ/hr Ethanol represents the GJ/hr Product Gas multiplied by the conversion efficiency of gas fermentation. The conversion efficiency of gas fermentation for the production of ethanol is approximately, fifty-five percent (55%), conservatively. With this conversion efficiency, the GJ/hr Ethanol was found to be 8.25. The current price of biogas where no renewable incentives exist is in the range of four dollars ($4) in the United States to ten dollars ($10) in the European Union, as of Nov. 5, 2018. For analysis purposes, a price of eight dollars per gigajoule biogas ($8/GJ Product Value) is used. The price of low carbon ethanol is currently, as of Nov. 5, 2018, $850/tonne ethanol in the European Union, $1100/tonne ethanol in China, and $1200/tonne ethanol in the United States. For analysis purposes, a price of $1000/tonne ethanol, equivalent to $37.30/GJ, is used. The $/hr Revenue is the GJ/hr Product Gas multiplied by the $/GJ Product Value. The % Revenue Gain is the comparative value of $/hr Revenue for the Anaerobic Digestion to Biogas versus the $/hr Revenue for the Gasification to Syngas. The $GJ Biomass Value illustrates the value of the biomass given the process selected. This is calculated by dividing the $/hr Revenue by the GJ/hr Biomass. As shown, the utilization of biomass to produce syngas through gasification greatly improves both revenue and value of the biomass.

An additional benefit of feeding the microbial biomass to the gasification process is that the microbial biomass may help provide supplementary amounts of syngas that may be needed in order to adequately supply the fermentation process. For example, a gasifier feed rate of approximately 1,200 dry tonnes per day, equivalent to 50 dry tonnes per hour, is required to supply the syngas needed for a 100,000 tonne/year ethanol production fermentation process, based upon current design parameters. The biomass produced by a fermentation process of this scale is typically between 1,000 and 1,200 kg/hr. This amount of biomass is substantial. The supplementary amounts of syngas that can be produced by gasification of biomass may be particularly beneficial in situations where gasifier feedstock is limited or where the feedstock price is high.

The biomass produced by the fermentation process may need an additional drying step before being passed to the gasifier in order to increase the percentage of biomass content. Depending on the requirements of the gasifier, the biomass may need to be dried to the point where the biomass makes up greater than 20 wt. %.

TABLE 3

| | GJ/hr Biomass | GJ/hr Product Gas | GJ/hr Ethanol | $/GJ Product Value | $/hr Revenue | % Revenue Gain | $GJ Biomass Value |
|---|---|---|---|---|---|---|---|
| Anaerobic Digestion to Biogas | 20 | 12 | n/a | 8 | 96.0 | n/a | 4.80 |
| Gasification to Syngas | 20 | 15 | 8.25 | 37.3 | 307.7 | 321% | 15.39 |

The calculations shown in the above table compare the conversion value of biomass to biogas, via anaerobic digestion, versus biomass to syngas, via gasification. The conversion efficiency of producing biogas from biomass via anaerobic digestion is approximately sixty percent (60%).

However, gasifying biomass with increased moisture content has the added benefit of increasing the H$_2$:CO ratio in the syngas produced. At approximately 15 wt. % moisture in the gasification feedstock, the resulting syngas stream comprises an H$_2$:CO ratio of 1:1. When the moisture in the gasification feedstock is increased to 40 wt. %, the resulting syngas stream comprises an $H_2$:CO ratio of 2:1. As previously stated, increased $H_2$:CO ratio in the syngas stream being fed to the fermentation process results in an increased efficiency of the fermentation process.

To achieve the aforementioned benefits the current disclosure recycles one or more of the following effluents selected from the group consisting of: biogas generated from a wastewater treatment process, tail-gas generated from the fermentation process, unused syngas generated by the gasification process, microbial biomass generated from the fermentation process, microbial biomass generated from a wastewater treatment process, crude ethanol from the product recovery process, fusel oil from the product recovery process, microbial biomass depleted water, wastewater generated from the fermentation process, and clarified water from a wastewater treatment process. One or more of these effluents may be sent to the gasification process to produce a syngas stream, used by the gasification process as a heating source, and/or used by the gasification process to quench the syngas produced. This syngas stream is preferably suitable for gas fermentation.

FIG. 1 shows a process integration scheme depicting the integration of a gasification process 300 having a dryer 10, a gas fermentation process 100, a product recovery process 400, and a wastewater treatment process 200, in accordance with one embodiment of the disclosure. These processes are integrated in a way that provides surprising synergies and advantages. The gasification process 300 receives a gasification feed 301, which may be any suitable material capable of being gasified to produce a syngas stream 302. In various instances, the gasification feed 301 is comprised at least partially of sorted and/or unsorted municipal solid waste. In other instances, the gasification feed 301 is comprised at least partially of forest and/or agricultural waste. In various instances, the gasification feed 301 is comprised at least partially of industrial solid waste. In particular embodiments, the gasification feed 301 is comprised of one or a combination of two or more of the following: sorted municipal solid waste, unsorted municipal solid waste, industrial solid waste, forest waste, agricultural waste, sludge derived from wastewater treatment, sewerage, lignocellulosic material, microbial biomass, at least one effluent from the fermentation process 100, at least one effluent from the product recovery process 400, and at least one effluent from the wastewater treatment process 200.

The gasification feed is dried in dryer 10 as part of the gasification process 300 in a gasifier. Dryer 10 operates using a dryer gas such as, for example, air, to dry the gasification feed. The dryer gas, such as air, is heated and in one embodiment, contacted with the gasification feed to dry the gasification feed. It is envisioned that, in other embodiments, the gasification feed may be heated without direct contact with the drying gas. The air, or other drying gas, may be heated by use of burners. The dryer gas in the dryer gas conduit 8 is in heat exchangeable communication with at least one burner. Fuel to the burners is provided by tail gas in conduits 104, 124, and 125.

The gasification process 300 receives the gasification feed 301 and produces a syngas stream 302 that is suitable for fermentation by a gas fermentation process 100. The fermentation process 100 utilizes this stream as a carbon source for producing one or more product, which may be at least partially contained in one or more effluent stream 102, 104. In various instances, the effluent from the fermentation process 100 is fermentation broth. One or more product produced by the fermentation process 100 is removed and/or separated from the fermentation broth by a product recovery process 400 in a product recovery unit. Preferably, the product recovery process 400 removes one or more product 406 and produces at least one effluent 402, 404, 408, which comprise reduced amounts of at least one product. This effluent may be sent via a conduit 402 to the wastewater treatment process 200 to produce at least one effluent 202 in a recycle conduit, which may be recycled to the gasification process 300 and/or the fermentation process 100.

An effluent from the fermentation process 100 is tail gas generated by the fermentation process 100. At least a portion of this tail gas is sent via a conduit 104, 124, and 125 to the gasification process 300 and used in dryer 10 as fuel for the burners of dryer 10 to heat a drying gas. In an optional embodiment, at least a portion of the tail gas may be sent by a conduit 124 to the gasification process 300 to be used as part of the gasification feed 301. In another optional embodiment, at least a portion of the tail gas may be sent via a conduit 114 to the gasification process 300 to quench the syngas stream 302.

In at least one embodiment, the effluent from the fermentation process 100 is fermentation broth. At least a portion of the fermentation broth is sent via a conduit 102 to the product recovery process 400. In at least one embodiment, the product recovery process 400 separates at least a portion of the microbial biomass from the fermentation process 100. In various embodiments, at least a portion of the microbial biomass that is separated from the fermentation broth is recycled to the fermentation process 100 via a conduit 404. In various embodiments, at least a portion of the microbial biomass that is separated from the fermentation broth is sent via a conduit 428 to the gasification process 300. At least a portion of the microbial biomass may be used as part of the gasification feed 301.

In various optional embodiments, at least a portion of a wastewater stream, comprising fermentation broth, which may contain microbial biomass, from the fermentation process 100 may be sent directly via a conduit 104 to the gasification process 300, without being passed to the product recovery process 400. At least a portion of the wastewater may be sent by a conduit 124 to the gasification process 300 to be used as part of the gasification feed 301. At least a portion of the fermentation broth may be sent via a conduit 114 to the gasification process 300 to quench the syngas stream 302.

In instances where the fermentation broth is processed by the product recovery process 400, at least a portion of the microbial biomass depleted water, produced through the removal of microbial biomass from the fermentation broth, may be returned to the fermentation process 100 via a conduit 404 and/or sent via a conduit 408 to the gasification process 300. At least a portion of the microbial biomass depleted water may be sent via a conduit 428 to the gasification process 300 to be used as part of the gasification feed 301. At least a portion of the microbial biomass depleted water may be sent via a conduit 418 to quench the syngas stream 302. Additionally, at least a portion of the effluent from the product recovery process 400 may be sent via a conduit 402 to the wastewater treatment process 200. Preferably, the effluent from the product recovery process 400 comprises reduced amounts of product and/or microbial biomass.

Preferably, the wastewater treatment process 200 receives and treats effluent from one or more process to produce clarified water. This clarified water can be sent via a conduit 202 to one or more process. In certain instances, at least a portion of the clarified water is sent via a conduit 212 to the fermentation process. At least a portion of the clarified water may be sent by a conduit 232 to the gasification process 300 to be used as part of the gasification feed 301. At least a portion of the clarified water may be sent via a conduit 222 to the gasification process 300 to quench the syngas stream 302.

In certain instances, the wastewater treatment process 200 generates microbial biomass as part of the treatment process. At least a portion of this microbial biomass may be sent via a conduit 232 to the gasification process 300. Preferably, the gasification process 300 utilizes at least a portion of the microbial biomass generated by the wastewater treatment process 200 as part of the gasification feed 301.

The wastewater treatment process 200, as a by-product of treating microbial biomass, produces biogas. At least a portion of this biogas can be sent via a conduit 202 to the gasification process 300. In certain instances, at least a portion of the biogas is sent via a conduit 232 to the gasification process 300 to be used as part of the gasification feed 301. At least a portion of the biogas may be sent via a conduit 222 to the gasification process 300 to quench the syngas stream 302.

Preferably, the gasification process 300 receives one or more effluent from the fermentation process 100, product recovery process 400, and/or the wastewater treatment process 200 and produces a syngas stream 302. This syngas stream 302 is preferably suitable to use as a feedstock for the gas fermentation process 100.

To be suitable to use as a feedstock for the gas fermentation process 100, the syngas stream 302 should preferably have a desired composition. In particular instances, the syngas 302 produced by the gasification process 300 contains one or more constituent that needs to be removed and/or converted.

Typical constituents found in the syngas stream 302 that may need to be removed and/or converted include, but are not limited to, sulphur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars. These constituents may be removed by one or more removal process.

Figure 2:
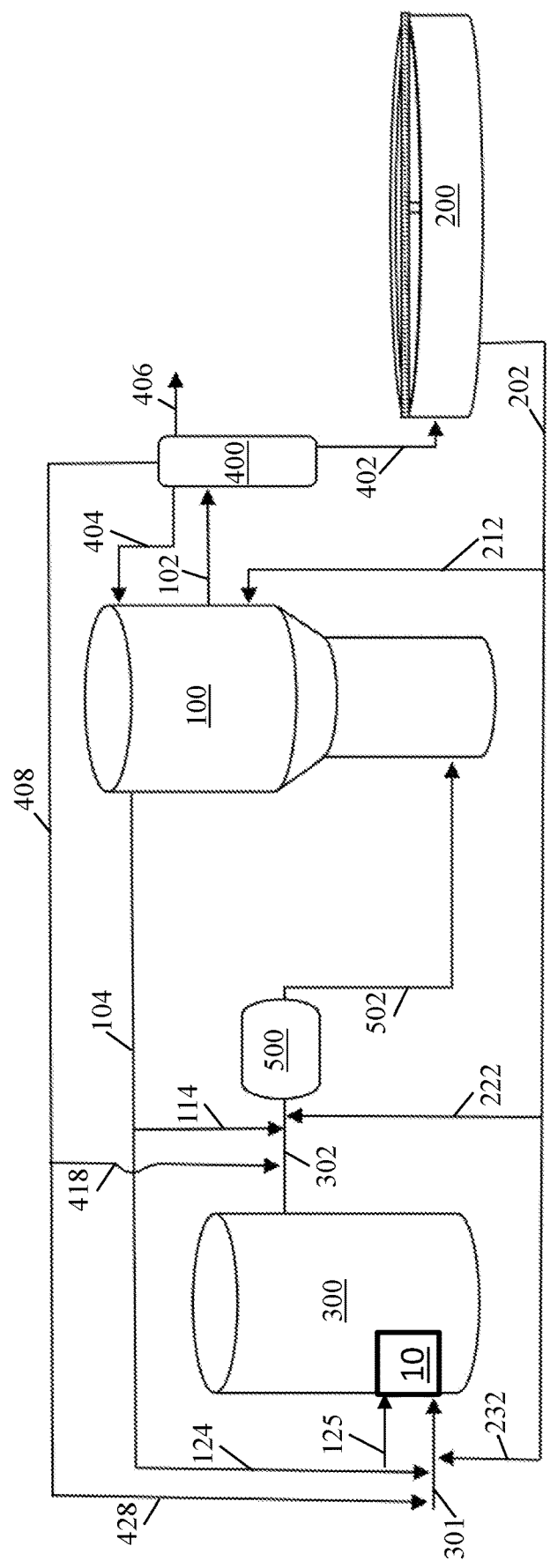
FIG. 2 shows the process integration scheme from FIG. 1, further comprising a removal process between the gasification process and the gas fermentation process, in accordance with one embodiment of the disclosure.

FIG. 2 shows the process integration scheme from FIG. 1, further comprising a removal process 500 between the gasification process 300 and the gas fermentation process 100, in accordance with one aspect of the disclosure.

Preferably, the removal process 500 comprises one or more of the following removal units: hydrolysis unit, acid gas removal unit, deoxygenation unit, catalytic hydrogenation unit, particulate removal unit, chloride removal unit, tar removal unit, and hydrogen cyanide polishing unit.

When incorporating a removal process 500, at least a portion of the syngas 302 from the gasification process 300 is sent to the removal process 500 to remove and/or convert at least a portion of at least one constituent found in the syngas stream 302. Preferably, the removal process 500 brings the constituents within allowable levels so as to produce a treated stream 502 suitable for fermentation by the fermentation process 100.

In various instances, the removal process 500 comprises two or more removal units selected from the group comprising: hydrolysis unit, acid gas removal unit, deoxygenation unit, catalytic hydrogenation unit, particulate removal unit, chloride removal unit, tar removal unit, and hydrogen cyanide polishing unit. In certain instances, one or more of these removal units are used to remove one or more constituent from the gas stream that may have adverse effects on downstream processes, for instance, the downstream fermentation process 100 and/or downstream removal units within the removal process 500.

One or more constituent removed and/or converted by the removal process 500 may be introduced and/or concentrated through the gasification of microbial biomass. In certain instances, the removal process 500 removes ammonia ($NH_3$) and/or hydrogen cyanide (HCN). This ammonia and/or hydrogen cyanide may be introduced and/or concentrated when the microbial biomass is gasified by the gasification process 300. Ammonia and hydrogen cyanide can be produced from the nitrogen contained within the microbial biomass, which will undergo reaction in the gasification process 300 to become $N_2$, $NH_3$, and trace HCN.

Typically, the syngas stream being fed to the fermentation process 100 is gaseous. However, the syngas stream may also be provided in alternative forms. For example, the syngas stream may be dissolved in a liquid saturated with the syngas, which may then be fed to the fermentation process 100. By way of further example, the syngas may be adsorbed onto a solid support.

Preferably the fermentation process 100 utilizes C1-fixing microorganisms to ferment the syngas stream 302 and produce one or more product. The C1-fixing microorganism in the fermentation process 100 is typically a carboxydotrophic bacterium. In particular embodiments, the carboxydotrophic bacterium is selected from the group comprising *Moorella, Clostridium, Ruminococcus, Acetobacterium, Eubacterium, Butyribacterium, Oxobacter, Methanosarcina, Methanosarcina*, and *Desulfotomaculum*. In various embodiments, the carboxydotrophic bacterium is *Clostridium autoethanogenum*.

In certain instances, the one or more of the processes are integrated through by utilizing at least a portion of at least one effluent from one process as a heating source for at least one other process.

Figure 3:
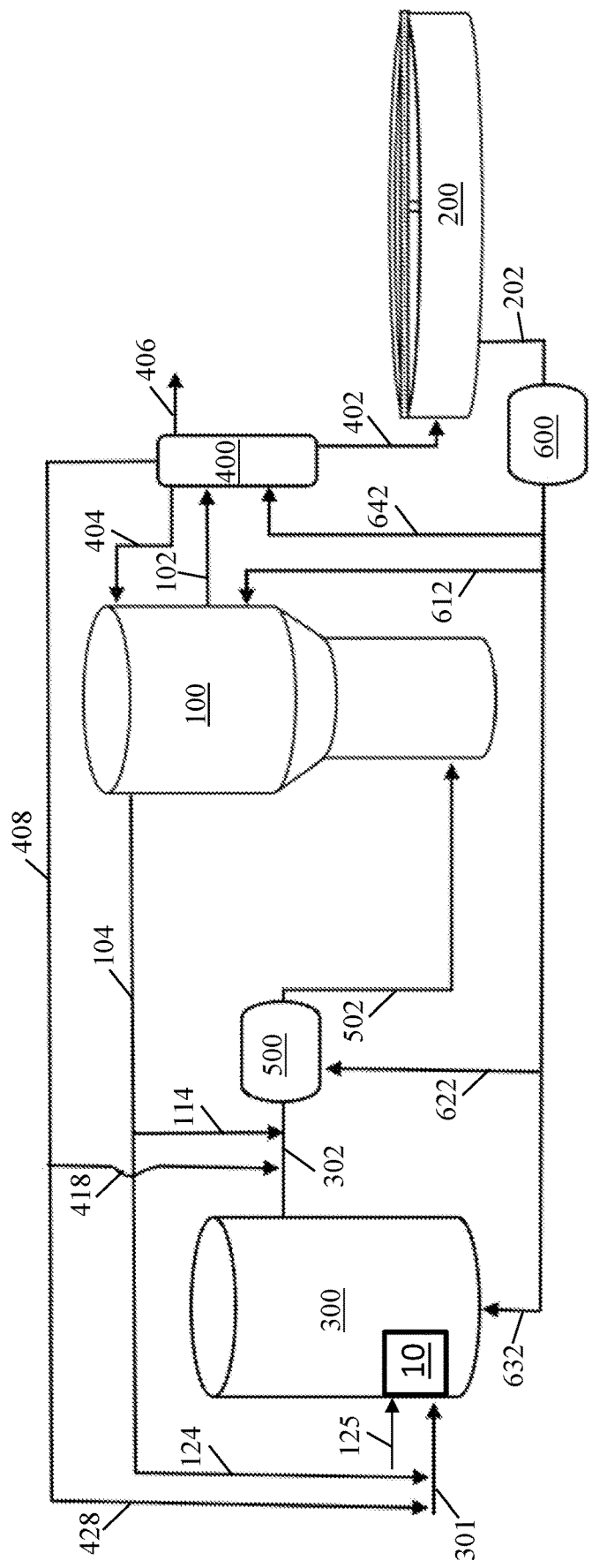
FIG. 3 shows the process integration scheme from FIG. 2, further comprising a removal process after the wastewater treatment process, in accordance with one embodiment of the disclosure.

FIG. 3 shows a process integration scheme depicting the integration of a gasification process 300, a gas fermentation process 100, a product recovery process 400, and a wastewater treatment process 200, in accordance with one aspect of the disclosure. In various instances, these processes are integrated by utilizing at least one effluent from at least one process as a heating source in at least one other process. In particular embodiments, the biogas generated by the wastewater treatment process 200 is utilized as a heating source for one or more process. Preferably, at least a portion of the biogas generated by the wastewater treatment process 200 is utilized as a heating source for the gasification process 300. In certain instances, the gasification process 300 utilizes at least a portion of the biogas generated by the wastewater treatment process 200 to melt at least a portion of a slag produced by the gasification process 300. In one or more embodiment, at least a portion of the biogas generated by the wastewater treatment process 200 is utilized as a heating source for the gas fermentation process 100. In one or more embodiment, at least a portion of the biogas generated by the wastewater treatment process 200 is utilized as a heating source for the product recovery process 400. In one or more embodiment, at least a portion of the biogas generated by the wastewater treatment process 200 is utilized as a heating source for the removal process 500.

In various instances, the biogas stream from the wastewater treatment process 200 is sent via a conduit 202 to at least one removal process 600 prior to being sent to one or more process. Preferably, the removal process 600 reduces the amount of at least one sulfur compound in the biogas stream.

When incorporating a removal process 600 following the wastewater treatment process 200, at least a portion of the biogas from the wastewater treatment process 200 is sent to the removal process 600 to remove and/or convert at least a portion of at least one constituent found in the biogas stream in a biogas treatment unit. Preferably, the removal process 600 brings the constituents within allowable levels so as to produce a treated stream 642, 612, 622, and/or 632 suitable to be used by the subsequent one or more process 400, 100, 500, and/or 300, respectively.

In particular embodiments, the tail-gas generated by the fermentation process 100 may also be used as a heating source for one or more process. For example, at least a portion of the tail-gas generated by the fermentation process 100 may be utilized as a heating source for the gasification process 300. In certain instances, the gasification process 300 utilizes at least a portion of the tail gas generated by the fermentation process 100 to melt at least a portion of a slag produced by the gasification process 300. In one or more embodiment, at least a portion of the tail gas generated by the fermentation process 100 is utilized as a heating source for the product recovery process 400. In various instances, the tail gas from the fermentation process 100 is sent to at least one removal process prior to being sent to one or more process.

In particular embodiments, unused syngas generated by the gasification process 300 is utilized as a heating source for one or more process. Preferably, at least a portion of the unused syngas generated by the gasification process 300 is utilized as a heating source for the gasification process 300. In certain instances, the gasification process 300 utilizes at least a portion of the unused syngas generated by the gasification process 300 to melt at least a portion of a slag produced by the gasification process 300. In one or more embodiment, at least a portion of the unused syngas generated by the gasification process 300 is utilized as a heating source for the product recovery process 400. In various instances, the unused syngas from the gasification process 300 is sent to at least one removal process prior to being sent to one or more process.

The fermentation process 100 is preferably capable of producing a variety of products. These products are preferably capable of being separated through use of a product recovery process 400. In various instances, at least a portion of at least one of the products produced by the fermentation process 100 may be used as a source for one or more process. In certain instances, at least a portion of the ethanol from the product recovery process 400 is utilized as a heating source for the gasification process 300. Preferably, the ethanol utilized as a heating source for one or more process is crude ethanol that does not meet the specification requirements for fuel-grade ethanol. In certain instances, the gasification process 300 utilizes at least a portion of the crude ethanol from the product recovery process 400 to melt at least a portion of a slag produced by the gasification process 300.

In certain instances, the fermentation process 100 produces fusel oil. This fusel oil may be recovered by the product recovery process 400 through any suitable means. For example, within the rectification column of a distillation setup. In at least one embodiment, at least a portion of the fusel oil from the product recovery process 400 is used as a heating source for one or more process. In certain instances, at least a portion of the fusel oil from the product recovery process 400 is utilized as a heating source for the gasification process 300. Preferably, the gasification process 300 utilizes at least a portion of the fusel oil from the product recovery process 400 to melt at least a portion of a slag produced by the gasification process 300.

A first embodiment includes a method comprising: a) heating a drying gas; b) providing the heated drying gas to a dryer containing a gasification feedstock to generate a dried gasification feedstock; c) gasifying at least a portion of the dried gasification feedstock to generate syngas; d) fermenting at least a portion the syngas in a bioreactor using a microorganism to generate at least one product and tail gas; and e) utilizing at least a portion of the tail gas to provide heat for heating the drying gas.

The method of the first embodiment may have the gasification feedstock as sorted municipal solid waste, unsorted municipal solid waste, industrial solid waste, agricultural waste, forest waste, microbial biomass, lignocellulosic material, sewerage, sludge from wastewater treatment, or any combination thereof.

The method of the first embodiment may have the tail gas comprises carbon dioxide. The tail gas may further comprise carbon monoxide, hydrogen, nitrogen, and methane.

The method of the first embodiment may have microorganism as one or more C1-fixing microorganism. The C1-fixing microorganism may be selected from *Moorella, Clostridium, Ruminococcus, Acetobacterium, Eubacterium, Butyribacterium, Oxobacter, Methanosarcina*, and *Desulfotomaculum*.

The gasification feedstock may be microbial biomass which may comprise one or more C1-fixing microorganism. The C1-fixing microorganism may be selected from *Moorella, Clostridium, Ruminococcus, Acetobacterium, Eubacterium, Butyribacterium, Oxobacter, Methanosarcina*, and *Desulfotomaculum*. The gasification feedstock may be microbial biomass which may be from a wastewater treatment plant.

The method of the first embodiment may have the drying gas be air.

The method of the first embodiment wherein the gasifying produces a greater yield of syngas as compared to gasifying without drying the gasification feedstock.

The method of the first embodiment wherein the gasifying produces a greater quality of syngas as compared to gasifying without drying the gasification feedstock.

The method of the first embodiment wherein the tail gas is burned to provide heat for heating the drying gas.

The method of the first embodiment wherein the tail gas is burned in a burner to provide heat for heating the drying gas.

A second embodiment includes an apparatus comprising: a) a dryer having one or more burners for heating a drying gas, the dryer in communication with a feedstock conduit; b) a gasifier in communication with the dryer; c) a bioreactor in fluid communication with the gasifier; d) a product conduit and a tail gas conduit in fluid communication with the bioreactor; and e) the tail gas conduit also in fluid communication with the one or more burners.

The apparatus of the second embodiment may further comprise a dryer gas conduit in communication with the dryer and in heat exchangeable communication with at least one burner.

The apparatus of the second embodiment may further comprise a product recovery unit in fluid communication with a wastewater treatment unit and a first recycle conduit from the wastewater treatment unit to the dryer. The apparatus may further comprise a biogas treatment unit in fluid communication with the first recycle conduit.

The apparatus of the second embodiment may further comprise a second recycle conduit from the product recovery unit to the dryer.

The of the second embodiment may further comprise at least one removal unit in fluid communication with at least the gasifier and the bioreactor.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavor in any country.

The use of the terms "a" and "an" and "the" and similar referents in the context of describing the disclosure (especially in the context of the following claims) are to be construed to cover both the singular and the plural unless otherwise indicated herein or clearly contradicted by context. The terms "comprising," "having," "including," and "containing" are to be construed as open-ended terms (e.g., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein is merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method comprising:
   a) heating a drying gas;
   b) providing the heated drying gas to a dryer containing a gasification feedstock, and directly contacting the drying gas with the gasification feedstock to generate a dried gasification feedstock;
   c) passing at least a portion of the dried gasification feedstock to a gasification process, and gasifying the dried gasification feedstock to generate syngas;
   d) fermenting at least a portion of the syngas in a bioreactor using a microorganism to generate tail gas, and a fermentation broth comprising at least one product and microbial biomass comprising the microorganism;
   e) passing the fermentation broth to a product recovery process to produce a microbial biomass depleted water stream, a crude ethanol stream, a fusel oil stream and a product stream, wherein microbial biomass comprising the microorganism is separated from the fermentation broth;
   f) drying at least a portion of the microbial biomass comprising the microorganism;
   g) passing at least a portion of the dried microbial biomass of step (f) to the gasification process gasifying the dried microbial biomass to generate syngas, and sending the syngas to the bioreactor of step (d), and further passing at least a portion of a stream selected from the microbial biomass depleted water stream, the crude ethanol stream, the fusel oil stream, and any mixture thereof to the gasification process; and
   h) utilizing at least a portion of the tail gas to provide heat for heating the drying gas.

2. The method of claim 1, wherein the gasification feedstock is sorted municipal solid waste, unsorted municipal solid waste, industrial solid waste, agricultural waste, forest waste, lignocellulosic material, sewerage, sludge from wastewater treatment, or any combination thereof.

3. The method of claim 1, wherein the tail gas comprises carbon dioxide.

4. The method of claim 3, wherein the tail gas further comprises carbon monoxide, hydrogen, nitrogen, and methane.

5. The method of claim 1, wherein the microorganism is one or more C1-fixing microorganism.

6. The method of claim 5, wherein the C1-fixing microorganism is selected from *Moorella, Clostridium, Ruminococcus, Acetobacterium, Eubacterium, Butyribacterium, Oxobacter, Methanosarcina, Desuljotomaculum*, and any combination thereof.

7. The method of claim 1, wherein the drying gas is air.

8. The method of claim 1, wherein the gasification process produces a greater yield of syngas as compared to gasification without drying the gasification feedstock.

9. The method of claim 1, wherein the gasification process produces a greater quality of syngas as compared to gasification without drying the gasification feedstock.

10. The method of claim 1, wherein the tail gas is burned to provide heat for heating the drying gas.

11. The method of claim 1, wherein the microbial biomass depleted water stream which is passed to the gasification process.

12. The method of claim 11, wherein the $H_2$:CO ratio of the syngas from the gasification process is increased to at least 2:1.

13. The method of claim 1, wherein at least 92% of energy in the tail gas is recovered.

14. A method comprising:
a) heating a drying gas;
b) providing the heated drying gas to dryer containing gasification feedstock, and directly contacting the drying gas with the gasification feedstock to generate a dried gasification feedstock;
c) passing at least a portion of the dried gasification feedstock to a gasification process, and gasifying the dried gasification feedstock to generate syngas;
d) fermenting at least a portion of the syngas in a bioreactor using a microorganism to generate tail gas, and a fermentation broth comprising at least one product and microbial biomass comprising the microorganism;
e) passing the fermentation broth to a product recovery process to produce a microbial biomass depleted water stream, a crude ethanol stream, a fusel oil stream and a product stream, wherein microbial biomass comprising the microorganism is separated from the fermentation broth;
f) drying at least a portion of the microbial biomass comprising the microorganism;
g) passing at least a portion of the dried microbial biomass of step (f) to the gasification process gasifying the dried microbial biomass to generate syngas, and sending the syngas to the bioreactor of step (d), and further passing at least a portion of a stream selected from the microbial biomass depleted water stream, the crude ethanol stream, the fusel oil stream, and any mixture thereof to the gasification process; and
h) utilizing at least a portion of the tail gas to provide heat for heating the drying gas;
i) generating a microbial biomass depleted water stream from the product recovery process and passing the microbial biomass depleted water stream to the gasification process thereby increasing the H2:CO ratio of the syngas from the gasification process to at least 2:1.

15. The method of claim 14, wherein at least 92% of energy in the tail gas is recovered.

16. A method comprising:
a) heating a drying gas;
b) providing the heated drying gas to dryer containing gasification feedstock, and directly contacting the drying gas with the gasification feedstock to generate a dried gasification feedstock;
c) passing at least a portion of the dried gasification feedstock to a gasification process, and gasifying the dried gasification feedstock to generate syngas;
d) fermenting at least a portion of the syngas in a bioreactor using a microorganism to generate tail gas, and a fermentation broth comprising at least one product and microbial biomass comprising the microorganism;
e) passing the fermentation broth to a product recovery process to produce a microbial biomass depleted water stream, a crude ethanol stream, a fusel oil stream and a product stream, wherein microbial biomass comprising the microorganism is separated from the fermentation broth;
f) drying at least a portion of the microbial biomass comprising the microorganism;
g) passing at least a portion of the dried microbial biomass of step (f) to the gasification process gasifying the dried microbial biomass to generate syngas, and sending the syngas to the bioreactor of step (d), and further passing at least a portion of a stream selected from the microbial biomass depleted water stream, the crude ethanol stream, the fusel oil stream, and any mixture thereof to the gasification process; and
h) utilizing at least a portion of the tail gas to provide heat for heating the drying gas wherein at least 92% of energy in the tail gas energy is recovered.

17. The method of claim 16, wherein the microbial biomass depleted water stream is passed to the gasification process.

18. The method of claim 17, wherein the $H_2$:CO ratio of the syngas from the gasification process is increased to at least 2:1.

* * * * *